United States Patent [19]
Machemer et al.

[11] Patent Number: 5,638,149
[45] Date of Patent: Jun. 10, 1997

[54] MOTORIZED APPLANATION TONOMETER

[75] Inventors: Robert Machemer; Dyson Hickingbotham, both of Durham, N.C.

[73] Assignee: Duke University, Durham, N.C.

[21] Appl. No.: 531,330

[22] Filed: Sep. 20, 1995

[51] Int. Cl.[6] .................. A61B 3/00; A61B 3/16
[52] U.S. Cl. ............................. 351/200; 128/645
[58] Field of Search ..................... 351/200, 205; 128/645, 646, 652; 318/2, 9

[56] References Cited

U.S. PATENT DOCUMENTS

| | | | |
|---|---|---|---|
| 3,934,462 | 1/1976 | Rende | 73/80 |
| 4,660,465 | 4/1987 | Jentzsch et al. | 98/115.4 |
| 4,874,236 | 10/1989 | Abraham | 351/205 |
| 4,987,899 | 1/1991 | Brown | 128/645 |
| 5,203,331 | 4/1993 | Draeger | 128/652 |
| 5,363,155 | 11/1994 | Urinowski et al. | 351/205 |

*Primary Examiner*—Huy Mai
*Attorney, Agent, or Firm*—Nixon & Vanderhye PC

[57] ABSTRACT

A control unit may be mounted in operative relationship to a conventional tonometer adjustment wheel to allow for motorized adjustment thereof. The unit includes a battery which powers a DC motor. The motor provides driven input to a right-angle gear drive, the output of which drives a friction wheel. The friction wheel is positioned so as to be in frictional engagement with the outer circumferential surface of the tonometer adjustment wheel. Actuation of a remote-mounted switch therefore allows the attending ophthalmologist to selectively drive the tonometer adjustment wheel in clockwise and counterclockwise directions so as to thereby adjust tonometer settings. The gear drive is mounted for pivotal movements about an axis transverse to the rotational axis of the tonometer adjustment wheel so that the friction wheel may be moved between engaged and disengaged positions relative to the tonometer adjustment wheel. A spring normally biases the friction wheel into its engaged position with the tonometer adjustment wheel.

10 Claims, 2 Drawing Sheets

MOTORIZED APPLANATION TONOMETER

FIELD OF INVENTION

The present invention relates generally to ophthalmic instruments. In preferred embodiments, the present invention relates to applanation tonometers having motorized adjustment capabilities.

BACKGROUND AND SUMMARY OF THE INVENTION

Tonometers are well known ophthalmic instruments which are used to measure the intraocular pressure of a patient's eye. During the intraocular pressure measurement procedure, however, the attending ophthalmologist must make required adjustments in the tonometer and/or a control lever for the instrument's microscope eyepiece. Typically, these manual control inputs must occur while the ophthalmologist also holds the patient's eyelids apart.

One prior proposal to alleviate some of the control/adjustment awkwardness of conventional applanation tonometers is disclosed in U.S. Pat. No. 5,363,155 to Urinowski et al (the entire content of which is expressly incorporated hereinto by reference). The apparatus disclosed in FIG. 7 of Urinowski et al '155 includes a remote-control motorized unit which may be coupled operatively to the adjustment knob of the tonometer unit via a flexible drive shaft. Operation of the selector switch will thus cause the motor in the unit to drive, via the flexible shaft, the adjustment wheel. (See column 5, lines 22–30.)

SUMMARY OF THE INVENTION

The present invention is embodied in a unit which may be mounted in operative relationship to a conventional tonometer adjustment wheel. As such, the unit of this invention is particularly adapted for use in retrofitting existing tonometers, but could be supplied as original equipment on newly manufactured tonometers.

The unit includes a battery which powers a DC motor. The motor provides driven input to a right-angle gear drive, the output of which drives a friction wheel. The friction wheel is positioned so as to be in frictional engagement with the outer circumferential surface of the tonometer adjustment wheel. Actuation of a remote-mounted switch therefore allows the attending ophthalmologist to selectively drive the tonometer adjustment wheel in clockwise and counterclockwise directions so as to thereby adjust tonometer settings.

The gear drive is mounted for pivotal movements about an axis transverse to the rotational axis of the tonometer adjustment wheel so that the friction wheel may be moved between engaged and disengaged positions relative to the tonometer adjustment wheel. A spring normally biases the friction wheel into its engaged position with the tonometer adjustment wheel.

The friction drive wheel may be maintained in its disengaged position against the bias force of the spring, however, by means of a friction drive release. In the disclosed embodiment, the friction drive release is comprised of an aperture which receives a pin when the friction drive wheel is in its disengaged position. The pin thus serves as a stop element against which a bracket under influence of the spring bias force rests.

Further aspects and advantages of this invention will become more clear after careful consideration is given to the following detailed description of the preferred exemplary embodiment thereof.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
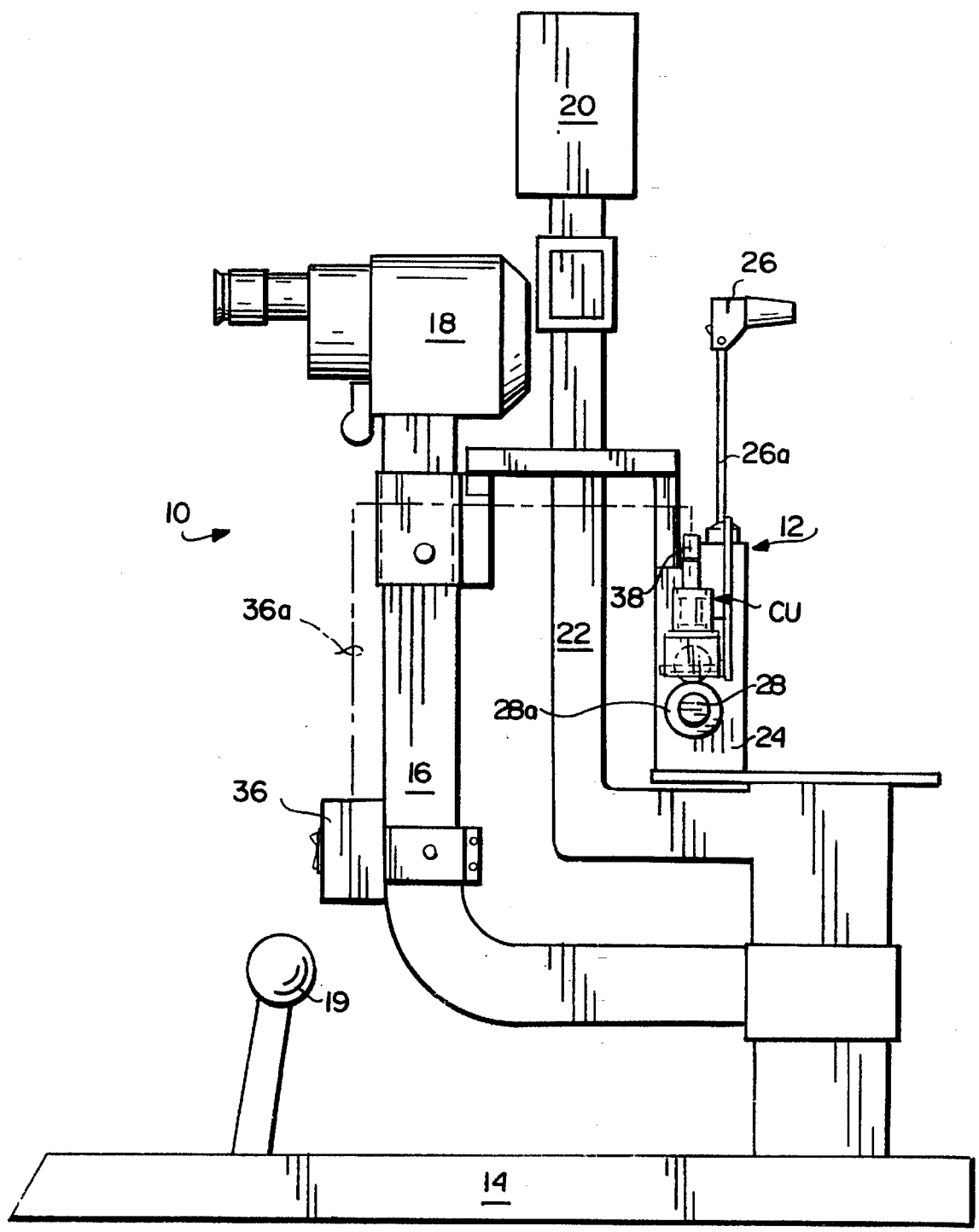
FIG. 1 is a side elevation view showing an applanation tonometer which includes the motorized adjustment unit of this invention.

Accompanying FIG. 1 shows a conventional slit lamp apparatus 10 equipped with a conventional tonometer unit 12 for measuring intraocular pressure of a patient's eye. Slit lamp apparatus 10 includes a base 14 supporting an arm 16 carrying a microscope eyepiece 18 at its upper end forwardly of the apparatus enabling an ophthalmologist to view a patient's eye rearwardly of the tonometer unit 12. A control lever 19 controls the position of the arm 16, and thereby of the microscope eyepiece 18. A lamp unit 20 is carried at the upper end of a lamp arm 22 between the microscope eyepiece 18 and the tonometer unit 12 for illuminating the eye of the patient.

The tonometer unit 12 includes a housing 24 mounted forwardly of the slit lamp unit 20 and carries a contact element in the form of a prism 26 at the terminal end of a sensing arm 26a. The contact element 26 is thus adapted to be brought into contact with the cornea of the patient's eye. Contact prism 26 is adjustable, via rotary adjusting knob 28 positioned at the lower end of the housing 24. The knob 28 may be manually rotated in order to move the sensing arm 26a, and hence the contact prism 26, towards or away from the patient's eye to vary the pressure of the prism 26 on the patient's eye during the intraocular pressure examination. An indicia wheel 28a is concurrently rotated with knob 28 so as to cooperate with calibration markings (not shown) on the housing 24. In such a manner, the indicia wheel 28a indicates the amount of rotation of knob 28, and thereby the pressure applied by the contact prism 26 to the patient's eye.

Figure 2:
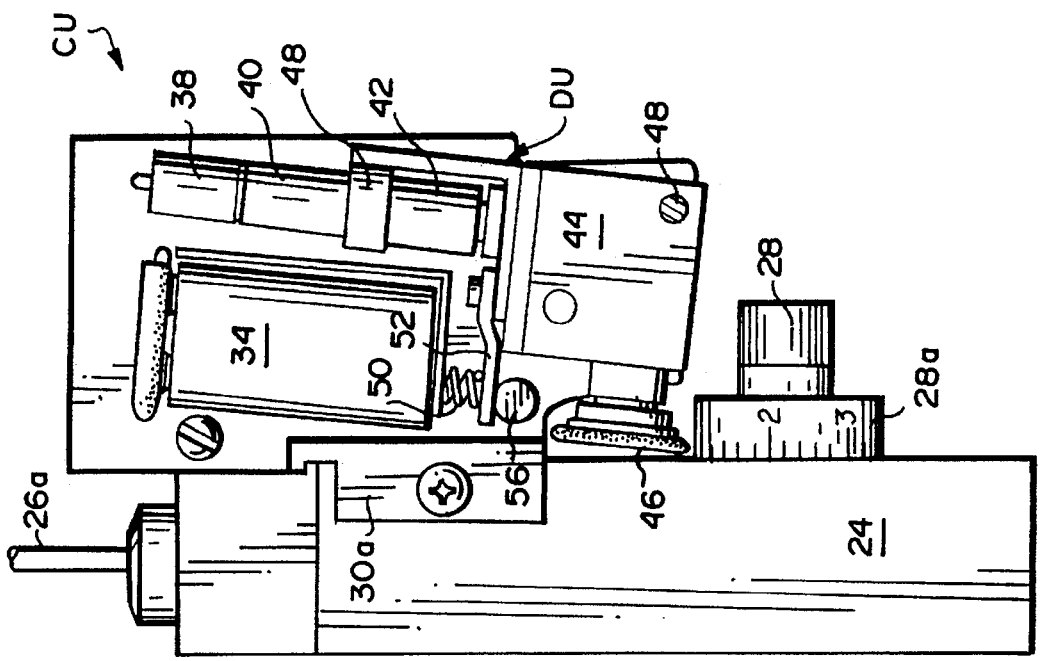
FIG. 2 is an enlarged elevation view as taken along line II—II in FIG. 1, showing the friction wheel of the adjustment unit engaged with the adjustment knob of the tonometer.
Figure 3:
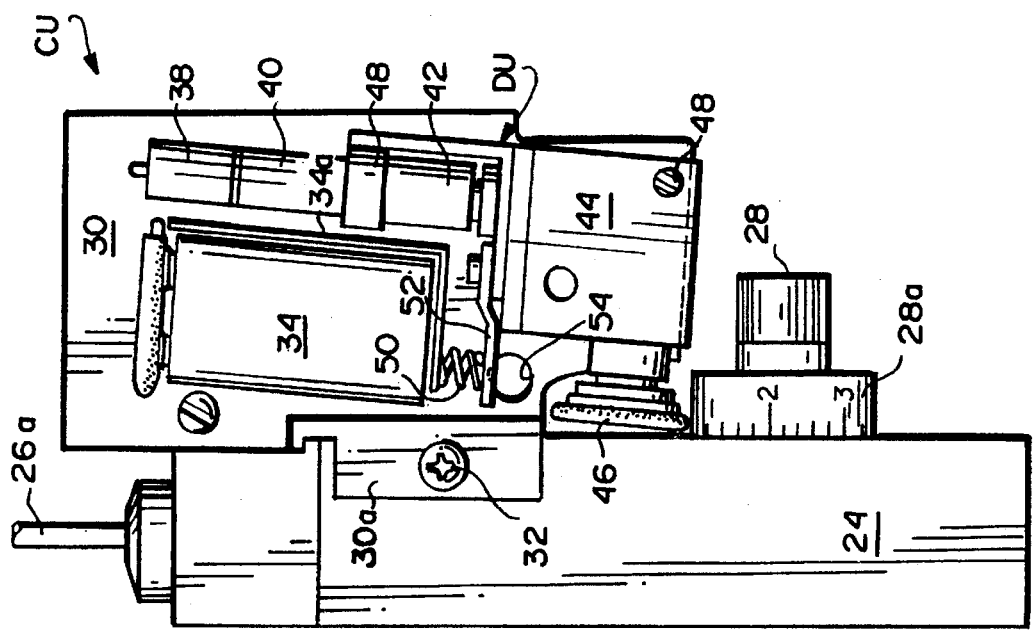
FIG. 3 is an enlarged elevational view similar to FIG. 2, but showing the friction wheel of the adjustment unit in a disengaged relationship with the adjustment knob of the tonometer.

According to the present invention, a self-contained motorized adjustment control unit CU is attached to the housing 24 as is perhaps more clearly shown in FIGS. 2 and 3. In this regard, the control unit CU includes a support plate 30 having a mounting flange 30a which is rigidly mounted to the tonometer housing 24 via any suitable means (e.g., a screw 32).

A conventional DC battery 34 (e.g., a conventional 9 volt DC battery) is mounted to the support plate 30 by a right angle battery mounting bracket 34a. The battery 34 is electrically connected to a switch 36 via wiring 36a (see FIG. 1) and a reversible DC drive motor 38 (via wiring not shown). The motor 38 is, in turn, mechanically connected to a transmission member 40 which drives a coupling 42. The motor-driven output of the coupling 42 is thus received as an input to a right angle gear unit 44 which rotates a friction wheel 46 about an axis which is normal to the input axis of the drive unit 44. The drive motor 38, transmission member 40 and coupling 42 are coaxially mounted as a unit with the right angle gear unit 44 via bracket member 48, and will hereinafter be referred to as the drive unit DU. Although a DC motor and its associated circuitry are preferred, the present invention could likewise be supplied with a suitable AC motor, switch, etcetera.

The drive unit is mounted to the support plate 30 for pivotal movements about pivot pin 48 passing through the right angle gear unit 44. Thus, the drive unit DU is capable of pivoting about the pivot pin 48 so that the friction wheel 46 may be moved into and out of contact with the indicia wheel 28a of knob 28 as shown in FIGS. 2 and 3, respectively. The friction wheel 46 can be provided with any suitable friction material (e.g., and elastomeric material) about its circumferential edge surface so as to ensure that positive engagement ensues with the indicia wheel 28a. Thus, upon actuation of switch 36 by the attending ophthalmologist, the friction wheel 46 will turn in one or another of its rotational directions so as move the indicia wheel 28, and hence the knob 28 in a desired direction so as to permit selective adjustment of the tonometer 12 and, particularly, the contact prism 26.

The drive unit DU is biased into the position shown in FIG. 2 (i.e., a position whereby the friction wheel 46 contacts the indicia wheel 28a) by means of compression spring 50 acting between the battery bracket 34a and the pivot lever 52. In order to maintain the control unit in the position shown in FIG. 3 (i.e., in a position whereby the friction wheel 46 is physically disengaged from the indicia wheel 28a), an aperture 54 is formed in the support plate 30 near the pivot lever 52. Thus, by manually inserting a stop pin 56 into the aperture 54, the terminal end of the pivot lever will be moved against the bias force of the spring 50 and will rest upon the pin 56 so as to maintain the friction wheel 46 in its disengaged position and allow manual adjustment of the tonometer knob 28 to occur. Thus, according to the present invention, the tonometer 12 can easily be converted between motorized and manual adjustments simply by pivoting the drive unit DU as described above.

While the present invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A drive unit to allow for motorized adjustment of an adjustment knob of an applanation tonometer, said drive unit comprising:

a motor having a driven output shaft;

a friction wheel having a circumferential region formed of a friction material which is engageable with an outer surface of the adjustment knob of the applanation tonometer;

a drive coupling which couples said driven output shaft of said motor and said friction wheel so that said friction wheel is driven by operation of said motor; and mounting structure for pivotally mounting said friction wheel proximity to the adjustment knob of the applanation tonometer so as to allow said friction wheel to be pivotally moved between (i) an engaged position with the adjustment knob wherein selective operation of said motor responsively causes said friction wheel to turn the adjustment knob and thereby allow motorized adjustment of the applanation tonometer, and (ii) a disengaged position wherein said friction wheel is disengaged from said adjustment knob to thereby prevent motorized adjustment of the applanation tonometer.

2. The drive unit as in claim 1, further comprising a spring biasing assembly for biasing said drive unit in a direction causing said friction wheel to be moved into said engaged position thereof.

3. The drive unit as in claim 2, wherein said spring biasing assembly includes a pivot lever, and a spring element operating on said pivot arm.

4. The drive unit as in claim 3, wherein said mounting structure includes an aperture adjacent said pivot lever, and a stop pin insertable into said aperture, said pivot lever bearing against said pivot pin when inserted into said aperture to prevent said friction wheel from pivotally moving from said disengaged position and into said engaged position thereof.

5. The drive unit as in claim 1, further comprising a DC battery electrically coupled to said motor.

6. A control unit for providing motorized adjustment of an adjustment knob of an applanation tonometer, said drive unit comprising:

(A) a drive unit which includes, a motor having a driven output shaft; a friction wheel having a circumferential region formed of a friction material which is engageable with an outer surface of the adjustment knob of the applanation tonometer;

a drive coupling which couples said driven output shaft of said motor and said friction wheel so that said friction wheel is driven by operation of said motor; and mounting structure for pivotally mounting said friction wheel in proximity to the adjustment knob of the applanation tonometer so as to allow said friction wheel to be pivotally moved between (i) an engaged position with the adjustment knob wherein selective operation of said motor responsively causes said friction wheel to turn the adjustment knob and thereby allow motorized adjustment of the applanation tonometer, and (ii) a disengaged position wherein said friction wheel is disengaged from said adjustment knob to thereby prevent motorized adjustment of the applanation tonometer; and (B) a switch unit coupled electrically to said motor for operating the motor and thereby allowing controlled motorized adjustment of the adjustment knob when said friction wheel is in said engaged position.

7. The control unit as in claim 6, wherein said drive unit includes a DC battery electrically coupled to said switch unit and said motor.

8. The control unit as in claim 6, further comprising a spring biasing assembly for biasing said drive unit in a direction causing said friction wheel to be moved into said engaged position thereof.

9. The control unit as in claim 8, wherein said spring biasing assembly includes a pivot level, and a spring element operating on said pivot arm.

10. The control unit as in claim 9, wherein said mounting structure includes an aperture adjacent said pivot lever, and a stop pin insertable into said aperture, said pivot lever bearing against said pivot pin when inserted into said aperture to prevent said friction wheel from pivotally moving from said disengaged position and into said engaged position thereof.

* * * * *